United States Patent [19]

Conte et al.

[11] Patent Number: 5,246,697

[45] Date of Patent: Sep. 21, 1993

[54] USE OF SUCRALFATE HUMID GEL AS VEHICLE FOR DRUGS HAVING TOPIC ACTIVITY AND FOR COSMETICS

[75] Inventors: Ubaldo Conte, Busto Arsizio; Paolo Colombo, Pavia; Giorgio Zagnoli, Como; Carla Caramella, Pavia, all of Italy

[73] Assignee: Laboratorio Italiano Biochimico Farmaceutico Lisapharma S.p.A., Italy

[21] Appl. No.: 538,739

[22] Filed: Jun. 15, 1990

[30] Foreign Application Priority Data

Jun. 16, 1989 [IT] Italy .............................. 20898 A/89

[51] Int. Cl.⁵ .................. A61K 31/74; A61K 9/14; A61K 9/70
[52] U.S. Cl. ......................... 424/78.03; 424/78.02; 424/443; 424/484; 424/486; 424/488; 514/887; 514/944
[58] Field of Search ................ 424/63, 443, 484, 486, 424/488, 78.02, 78.03; 514/887, 944

[56] References Cited

U.S. PATENT DOCUMENTS

| | | |
|---|---|---|
| 4,772,470 | 9/1988 | Inoue ..................... 424/81 |
| 4,795,436 | 1/1989 | Robinson ............... 424/457 |
| 4,853,227 | 8/1989 | Kurihara-Bergstrom ......... 424/489 |
| 4,910,023 | 3/1990 | Botzolakis .............. 424/470 |
| 4,937,079 | 6/1990 | Farolfi ..................... 424/485 |
| 4,945,085 | 6/1990 | Steiner .................... 514/23 |

FOREIGN PATENT DOCUMENTS

| | | |
|---|---|---|
| 286978A | 10/1988 | European Pat. Off. . |
| 0403048 | 12/1990 | European Pat. Off. . |
| 3434707 | 4/1985 | Fed. Rep. of Germany . |
| 2646604 | 11/1990 | France . |
| 107209A | 5/1984 | Japan . |
| 8905645 | 6/1989 | World Int. Prop. O. . |

*Primary Examiner*—Thurman K. Page
*Assistant Examiner*—Carlos Azpuru
*Attorney, Agent, or Firm*—Birch, Stewart, Kolasch & Birch

[57] ABSTRACT

The use of sucralfate humid gel is described as vehicle for the application of drugs having topic activity (dermic and mucosal) and as basis for the formulation of beauty masks and other cosmetic preparations. Therapeutic and cosmetic formulations are described in the form of creams, ointments, aqueous dispersions comprising sucralfate humid gel.

3 Claims, No Drawings

USE OF SUCRALFATE HUMID GEL AS VEHICLE FOR DRUGS HAVING TOPIC ACTIVITY AND FOR COSMETICS

DESCRIPTION

Sucralfate is a basic sucrose octasulphate aluminum salt which is used in medicine for the treatment of gastric and duodenal ulcers by oral administration.

In this area of the digestive system, sucralfate, after interaction with the gastric juice present in the stomach, forms an adhesive paste capable of tenaciously sticking to the gastro-duodenal wall protecting it from the insults of the gastric juices. This action is particularly evident in regard of the ulcered mucous membrane.

The pharmaceutical preparations, both liquid and semi-solid, employed in administering sucralfate are prepared in general by dispersion of the active principle in the form of micronized powder in an aqueous vehicle.

This physical form shows a dimensional distribution of the particles very much shifted toward the low values; however, it does not show values of the surface area as high as the ones of sucralfate humid gel which is an object of applicant's European patent 286.978.

In said patents a process is described for the preparation of a solid form of sucralfate as a powder which shows physical properties particularly suitable for the preparation of stable aqueous suspensions. Said particular physical form is defined sucralfate humid gel, as it contains a large amount of water and, once dispersed in water, produces a gel of considerable consistency.

Sucralfate humid gel to be used in the present invention has a water content of between 20 and 85% by weight, preferably between 60 and 85%.

It has the following granulometric characteristics: average diameter of the particles: 3 to 4 microns on the base of the ratio volume/surface (less than 6) with at least 50% by wt. below 5 microns; specific surface area (Lox method—Am. Soil Sci. Soc., I 44, 607, 1980) higher than 200 $m^2/g$.

It is prepared, according to the description in the above cited patent of the applicant, by dissolving sucralfate powder of the known commercial type in an aqueous solution of hydrochloric or sulphuric acid and adding then gradually NaOH aqueous solution to a pH of $4 \div 4.5$. The gel which results is washed with water and centrifuged.

Recently, the use of sucralfate in topic skin applications and for the treatment of phlogoses or lesions of anatomical districts different from the gastro-intestinal tract was claimed in the PCT/DK88/00216 patent application.

In said patent, the sucralfate formulations for topic use are prepared starting from a micronized powder and require, to attain the semi-solid consistency, the use of excipients of the pharmaceutical classes of emulsifiers, stabilizers and viscosity and suspension aids. The list of said excipients, the use of which is necessary for obtaining a preparation for topic applications, as reported on page 10 of the cited patent, comprises a large variety of polymeric substances or of substances of a colloidal nature.

Furthermore, as reported on page 11 of the patent, "a suitable starting material for the preparation of an ointment, paste, lotion, cream, suspension or gel is a micronized suspension of sucralfate".

The new physical form of sucralfate defined as humid gel shows a favourable sizes distribution of the solid particles and an absolutely peculiar rheology characterized by an evident antithixotropy. The peculiarity of the aqueous suspension rheology derives form the strong interaction between the sucralfate particles which develops when it is prepared according to the previously cited applicant's patent.

Said properties allow the direct preparation of a semi-solid form without the use of any excipient of the classes of viscosity and suspension aids etc., and without the need of a milling or micronizing process. Sucralfate humid gel shows in practice colloidal properties, in the aqueous suspensions.

We now have found that, from the biological standpoint, the colloidal properties of sucralfate humid gel in suspension, and in particular its rheology, bring about an extremely tenacious adhesion to the biological tissues which greatly favors, for instance, the anti-ulcer activity through a mechanism of protection of the mucous membranes.

This bio-adhesivity of sucralfate humid gel is absent in sucralfate powder of commercial grade and is indepedent from the presence of gastric juice.

Contrary to what reported in the patent JP 187614/82 of Oct. 27, 1982, where it is emphasized that sucralfate forms an adhesive paste which binds to the ulcer sites in the presence of gastric juice at a pH below 4, we have found that sucralfate humid gel shows a capacity of bio-adhesion or adhesion to biological tissues also at pH values higher than 4 and independently from the presence of gastric juice. This completely unexpected bioadhesion phenomenon allows the use of sucralfate humid gel, prepared according to the process described in the European patent 286,978, as base substance capable of adhering to tissues even in the absence of gastric juice, which is capable of transforming normal sucralfate powder in an adhesive paste.

The present invention refers therefore to the use of sucralfate humid gel as prepared according to the European patent 286,978, as a bio-adhesive substance capable of adhering to biological tissues even at a pH higher than 4, thus acting as a vehicle, support or main constituent for the preparation of semi-solid pharmaceutical substances.

We have found further that the product, because of its natural adhesivity and consistency, when applied as a thin layer on the skin, covers the area in a continuous and homogeneous manner and that this layer goes through a drying process which increases its consistency, leading to the formation of an artificial crust which exerts a protective action similar to the one of an eschara.

We have also found that the physical form of sucralfate humid gel favours the formation of emulsions of large amounts of oily substances without the aid of tensioactive agents. In practice, it was found convenient, in many cases, to use small amounts of tensioactive substances to facilitate the subsequent removal of the dried layer by washing with water.

We claim therefore the capacity of sucralfate humid gel suspensions of acting as vehicle for e.g. anti-phlogistic and antibiotic drugs.

Finally, sucralfate humid gel, always by virtue of its colloidal and rheological properties, may form the basis for the preparation of cosmetic formulations in which a capacity as vehicle, emulsifier and suspending agent is required.

In consideration of the bioadhesive properties and of the drying capacity of the suspension of sucralfate humid gel also its use for the preparation of cosmetic formulations such as beauty masks and others is claimed.

By virtue of its properties, sucralfate humid gel may thus be advantageously used in therapeutic or cosmetic formulations in the form of creams, pastes or liquid aqueous dispersion where bioadhesivity is required.

The amount of sucralfate present in said formulations is in general comprised between 5 and 30% by weight.

The advantages of the present invention are described herein below by means of formulation examples which, however, should not be intended as limiting the scope of the invention.

EXAMPLE 1

Sucralfate humid gel as vehicle for Amikacin sulphate (common name for 1-N-[L(−)-4-amino-2-hydroxybutyryl]kanamycin A, used as sulfate).

Mix 250 g sucralfate humid gel (containing 18.6% sucralfate) with 200 g glycerine FU IX and 30 g Etilon R 40 (Henkel, Duesseldorf) (Product obtained by esterifying castor oil with polyethylene glycol) in a planetary ointment mixer. Add 40 ml 250 mg/ml Amikacin solution and 470 g distilled water. Mix thoroughly and homogenize in a roller mill.

The gel obtained is filled into small aluminum tubes and sterilized by gamma rays.

The described sucralfate preparation when submitted to accelerated stability tests did not show any variations as to appearance, consistency or active principle content.

The preparation has the consistency of a fluid translucent cream, which can be easily squeezed out of the tube, and which, however, when put on the skin forms a rather consistent layer which tenaciously adheres to it.

A few minutes after the application, the gel layer starts drying, fissuring on the surface but tenaciously adhering to the skin.

Washing with water favors the removal of the product.

10 patients showing varicose ulcers were treated topically once a day for 10 days with the described formulation.

Laboratory examinations showed that the product is perfectly tolerated.

The therapeutic efficiency of the product was evaluated by clinical observation and laboratory tests on the rate of re-hepitelization and by evaluation of the pain, of the inflammatory process and of the sore extension and culture examination of the sore secretion prior to and after the treatment.

The obtained results show that the product has a marked therapeutic activity with respect to dermic ulcers and is remarkably well tolerated.

Comparison of the results obtained with the ones obtained by using Amikacin solution alone shows that the presence of sucralfate, allowing the permanence of the drug on the ulcerated area, accelerates the ulcer re-hepitelization.

EXAMPLE 2

Sucralfate in beauty masks 250 g sucralfate (as sucralfate humid gel) of the same type as used in Example 1 are mixed in a planetary mixer with 40 g glycerine FU 30 g Etilon R40 (Henkel-Duesseldorf, West Germany), 1 g lavander essence and 679 g distilled water. The mix is refined in a roller refiner until a translucent paste is obtained.

This preparation may also contain, dissolved in water, natural active principles having an eutrophic activity on the skin.

The preparation is applied on the facial surface in a layer approximately 0.5 cm thick and left there until almost complete water evaporation.

The water loss causes the hardening of the product layer.

The effect of the mask is due to the absorption capacity of sucralfate, to its effect on the cellular functions and to the removal process of the hardened mask.

The employed excipients, preventing a complete drying out of the mask, facilitate its removal.

In case of need, when no "peeling" action is required, the dried layer can be re-hydrated.

EXAMPLE 3

Sucralfate humid gel as greasy cream 150 g sucralfate (sucralfate humid gel, 18% sucralfate by wt.) are mixed with 147 g sorbitol 70% solution, in a planetary mixer. 22 g Etilon R40 and 147 g vaseline oil are added.

After making up the solution to 1 liter by addition of water, the mixture is homogenized and refined in a colloidal mill. The obtained gel is put into small aluminum tubes and sterilized with gamma rays. paste: it keeps homogeneous and stable for at least 24 months.

We claim:

1. A bio-adhesive composition for dermic use in therapeutic and/or cosmetic treatment, in the form of a gel, cream, paste or aqueous dispersion, which comprises:
   a) 1-N-[L(−)-4-amino-2-hydroxybutyryl]kanamycin A in a therapeutically effective amount for those in need thereof and
   b) a vehicle or support comprised of about 5 to 30% by weight of sucralfate humid gel, based on the total weight of said bio-adhesive composition, said sucralfate humid gel having an average particle diameter of less than 6 microns, a specific surface of at least 200 $m^2/g$ and a water content of between 20 and 85% by weight as determined when said sucralfate humid gel is in a powdery solid state prior to being combined with said 1-N-[L(−)-4-amino-2-hydroxybutyryl]kanamycin A.

2. Composition for cosmetic use according to claim 1, for application as a beauty mask.

3. A composition according to claim 1 wherein the sucralfate used as starting material has a water content between 60 and 85% by weight.

* * * * *